United States Patent [19]

Brust

[11] Patent Number: 5,914,243
[45] Date of Patent: Jun. 22, 1999

[54] PROCESS FOR THE IMMUNOCHEMICAL DETERMINATION OF AN ANALYTE

[75] Inventor: Stefan Brust, Marburg-Michelbach, Germany

[73] Assignee: Behring Diagnostics GmbH, Marburg, Germany

[21] Appl. No.: 08/441,175

[22] Filed: May 15, 1995

Related U.S. Application Data

[63] Continuation of application No. 08/069,432, Jun. 1, 1993, abandoned.

[30] Foreign Application Priority Data

Jun. 3, 1992 [DE] Germany ............................ 42 18 257

[51] Int. Cl.⁶ ..................................................... G01N 33/53
[52] U.S. Cl. ........................... 435/7.92; 435/7.1; 435/962; 436/518; 436/528; 436/531
[58] Field of Search ................................. 435/7.92, 7.94, 435/7.95, 962, 7.1; 436/518, 528, 531

[56] References Cited

U.S. PATENT DOCUMENTS

| | | | |
|---|---|---|---|
| 4,228,237 | 10/1980 | Hevey | 435/7.93 |
| 4,376,110 | 3/1983 | David et al. | 436/513 |
| 4,495,296 | 1/1985 | Neurath et al. | 435/7.94 |
| 4,743,542 | 5/1988 | Graham et al. | 435/7.94 |
| 5,011,771 | 4/1991 | Bellet et al. | 435/7.94 |
| 5,126,241 | 6/1992 | Schenk | 435/7.1 |

FOREIGN PATENT DOCUMENTS

| | | |
|---|---|---|
| 2008100 | 7/1993 | Canada . |
| 0 363 942 | 4/1990 | European Pat. Off. . |
| 0 379 216 | 7/1990 | European Pat. Off. . |
| 0 452 503 | 10/1991 | European Pat. Off. . |

*Primary Examiner*—Jeffrey Stucker
*Attorney, Agent, or Firm*—Finnegan, Henderson, Farabow, Garrett & Dunner, L.L.P.

[57] ABSTRACT

The invention relates to a process for the immunochemical determination of an analyte in a sample by means of a first specific binding partner, where the specific binding partner being immobilized on a support and the extent of the binding of the analyte to the specific binding partner being determined by means of a further specific binding partner which directly or indirectly bears a label, wherein there is additionally added to the process a binding factor, which is not labelled.

9 Claims, 2 Drawing Sheets

PROCESS FOR THE IMMUNOCHEMICAL DETERMINATION OF AN ANALYTE

This application is a continuation of the application Ser. No. 08/069,432, filed Jun. 1, 1993, now abandoned.

The invention relates to a process for the immunochemical determination of an analyte in a sample by means of a first specific binding partner, the specific binding partner being immobilized on a support and the extent of the binding of the analyte to the specific binding partner being determined by means of a further specific binding partner which directly or indirectly bears a label.

Customary immunological processes for diagnosing diseases which are accompanied by formation of specific antibodies against a disease-causing agent, such as viruses, bacteria, allergens, autoantigens or particular pharmaceuticals depend on the ability of these antibodies to form complexes with antigenic structures of the causative agent.

In some of these processes, generally designated as heterogeneous immunoassay, a sample which is to be examined for the content of, for example, specific antibodies (analyte antibodies) is brought into contact with antigenic structures of the disease-causing agent, these antigenic structures being immobilized on suitable known support materials. Analyte antibodies contained in the sample are bound as an immune complex to the antigenic structures of the disease-causing agent which are immobilized on the support material, and detected. For the detection, detection antibodies or other specific receptors, for example protein A, may be used which are able to form complexes with the analyte antibody of the sample.

As a rule, the detection reagent bears a label which permits measurement by instrumentation of the quantity of the bound specific antibody.

Common labels are: radioactive isotopes, enzymes, fluorescent, phosphorescent or luminescent substances, substances having stable unpaired electrons, erythrocytes, latex particles, magnetic particles and metal sols.

In these processes, both single-step and multi-step detection methods are known. Each process step is customarily terminated by a separation process (washing step).

In heterogeneous immunoassays, the technique of the single-step method, which is very simple to perform, is not, however, suitable for detecting all disease markers. For technical reasons, two-step or else multi-step processes must often be used.

These methods are very specific, but have the disadvantage, however, that the disease-causing agents to be detected, or antibodies directed against them, which have entered a complex with the immobilized specific receptor in the first process step, can partially dissociate again from the complex in the subsequent incubation steps, in a reverse reaction known to the person skilled in the art, and thereby elude the detection reaction, resulting, inter alia, in the sensitivity being markedly reduced.

The diagnostic efficiency of such multi-step processes is always particularly strongly reduced when the rate of the reverse reaction between immobilized receptor and agent to be detected is high. This is the case, for example, with low-affinity antibodies against disease-causing agents or against pharmaceuticals. These problems are also known particularly in the case of processes for detecting frequently mutating disease-causing agents or disease markers, which show lower interaction with the immobilized specific receptor after mutation. There was therefore the object of finding reagents which do not possess the indicated disadvantages.

Surprisingly, it was established that the rate of the reverse reaction is substantially reduced by addition of a binding factor against structural features of the agent to be detected. This binding factor must possess more than one site which is capable of binding the agent to be detected and must not interfere with the immunochemical detection of the agent.

The agent to be detected (analyte), in the sense of this invention, can be either an antibody which is induced, for example, by a disease-causing agent, or an antigen such as, for example, the disease-causing agent itself.

The invention therefore relates to a process for the immunological determination of one or more analytes by means of a specific binding partner, the specific binding partner being immobilized on a support and the extent of the binding of the analyte to the specific binding partner being determined by means of a further specific binding partner which directly or indirectly bears a label, wherein, in the process, a binding factor is additionally used which possesses more than one site which is capable of binding the agent to be detected, possesses no affinity for the immobilized specific binding partner, and is not labeled.

Figure 1:
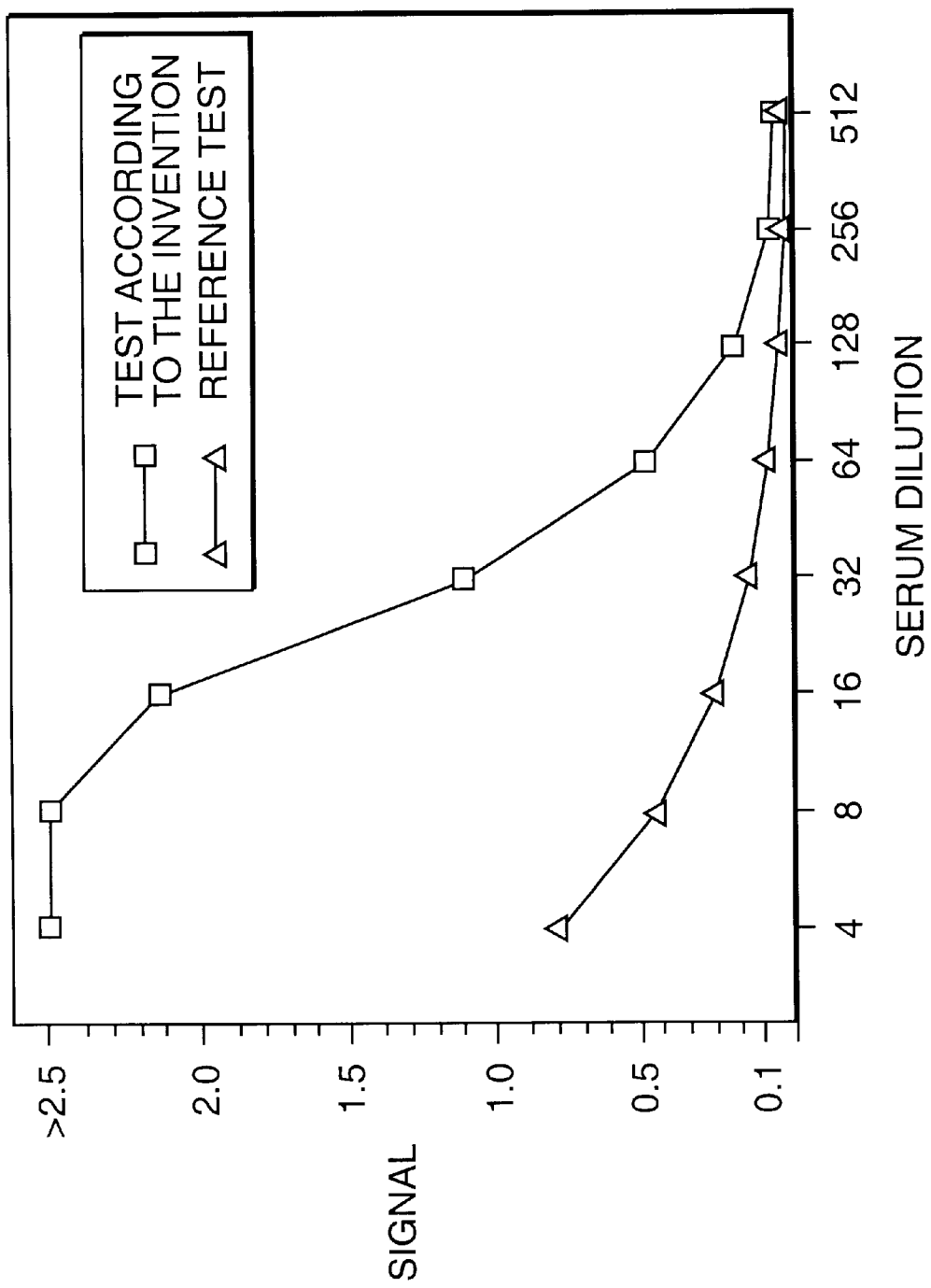
FIG. 1 depicts the titration curve of an anti-HIV 1 positive sample (#9804/50).

In this context, not labeled means that it bears either no label or at least not that label with which the extent of the binding of the analyte to the specific binding partner is determined.

In the sense of this invention, addition also denotes that the binding factor is immobilized on the solid phase in the relevant process steps or, in the case of the detecting agents based on matrix chemistry and known to the person skilled in the art, is already present on the, phase, having been dried into it.

The processes in which binding factors may be used are known per se in all their embodiments to the person skilled in the art. Among these processes are single-step and multi-step processes, with, in the case of the latter, a washing step being inserted as a rule between the individual steps.

It is important that the process according to the invention can be employed in a suitable form in all immunochemical processes in which, in a first step, an immunochemical or comparable binding of an analyte to a preferably immobilized, specific binding partner is effected, and, in a second, but not necessarily temporally separated, step a direct or indirect detection is effected.

Without thereby postulating a particular mode of action of the binding factors, it appears to be advantageous if the analyte, which may be a peptide or a protein, possesses, besides the binding sites for the specific solid phase binding partner and detection binding partner, at least one further epitope.

Preferably, the binding factors are employed in the processes known to the person skilled in the art as sandwich ELISA, an enzyme, preferably with a chromogenic or fluorogenic substrate or a chemiluminescent label, preferably being used as the abeling system. However, the embodiment of the detection method does not have a primary influence on the possible uses of the binding factors.

Microtiter plates, magnetic particles, latex particles or test elements based on matrix chemistry, such as, for example, fibers or test modules containing membranes, are preferably used as solid phases.

It is also known to the person skilled in the art that immunochemical processes as described above may also be employed for the simultaneous determination of different analytes, such as, for example, HIV 1/2 or HIV 1+2/HCV. Such embodiments are also included here.

Processes are advantageous in which the binding factor is added in the reaction step in which the analyte binds to the second, preferably labeled, specific binding partner.

The use of the binding factor has a particularly advantageous effect in multi-step processes, the binding factor preferably being added after the first washing step. In addition, the invention relates to a reagent for use in the abovementioned process which contains a binding factor.

Furthermore, the invention relates to the abovementioned process in which the binding factor is an antibody conjugate.

Binding factors, in the sense of the invention, are specific binding partners which possess more than one binding site with bioaffinity for the agent to be detected. A binding factor or components of this binding factor may be constituted by conjugates of the antibodies as well as the antibodies themselves. In the sense of this invention, antibodies are monoclonal or polyclonal antibodies as well as the known immuno-reactive fragments.

Lectins, or conjugates of a plurality of lectins, or conjugates of lectins with agent-specific antibodies or their fragments, are likewise suitable.

The binding factor can be added at any point in the respective reaction step of the determination; preferably, however, the addition is effected after the binding of the analyte to the solid phase.

Binding factors which are particularly preferred are antibodies against the specific immunoglobulin class of the antibody to be detected.

In the case of the antigen detection, the antibody used as a binding factor is preferably one which does not recognize the same epitope as the solid-phase antibody or the conjugate antibody.

A process is preferred in which at least one washing step is used.

Preferably, the binding factors are not homologous to the analyte antibodies. If the analyte antibody is a human antibody, mouse or rabbit antibodies or antibody conjugates, or conjugates of antibody fragments, are very particularly preferred.

Methods which are familiar to the person skilled in the art for preparing such conjugates, while preserving their bioaffinity function, are, for example, linking by means of chemical reagents or by means of interaction based on bioaffinity.

Hybrid molecules can also be produced by chemical synthesis, by the hybridoma technique, or by methods of gene technology. If a plurality of relevant agents (e.g. antibodies of the immunoglobulin classes G and M) against one or more defined disease-causing agents, e.g. against HIV 1 and HIV 2, are being detected, the binding factor can, for example, interact on a bioaffmity basis simultaneously with two or more agents.

The reagent according to the invention can be used in a multiplicity of processes within human and veterinary diagnostics. Examples which may be listed are two-step or multi-step tests for detecting antibodies of different immunoglobulin classes against structural features of viruses (e.g. viruses of the hepatitis A, B or C type as well as various HIV types), of bacterial and parasitic pathogens, and of allergic disorders. Additional examples are the detection of disease-causing agents such as viruses (e.g. hepatitis B virus), bacteria, parasites or allergens as well as of markers of diseases(e.g. tumor markers) in one-step or multi-step detection processes.

The invention is illustrated by the following example, without thereby being limited to it:

EXAMPLE a) Preparation of a reagent according to the invention 1 ml of 0.2 M LiBO3/20% dioxane is added to 4 mg of monoclonal anti-human IgG antibody (Fc-specific) in 1 ml of PBS, pH 7.2, and the mixture is treated with a 15-fold molar excess of N-γ-maleimidobutyrtyl-succinimide (GMBS) and incubated at room temperature for 1 h. The heterobifunctional reagent which remains unreacted is separated off by gel chromatography (Sephadex G-25) with 0.1 molar Na phosphate buffer +5 mmol/ml nitrilotriacetic acid (NTA), pH 6.0.

4 mg of monoclonal anti-human IgG antibody (Fc-specific) in 4 ml of 10 mmol/l sodium phosphate and 100 mmol/l NaCL pH 7.4, is incubated with a 24-fold molar excess of N-succinimidyl-3-(2-pyridyl-dithio)propionate (SPDP) at room temperature for 30 min., and then subsequently reduced with dithiothreitol (100-fold molar excess in relation to SPDP) at room temperature for 15 min. After reduction is complete, the low-molecular component is removed by gel filtration on Sephadex G-25 (0.1 M Na phosphate, 5 mmol/l NTA, pH 6.0).

The SH-activated anti-human IgG is incubated with the maleimide-activated anti-human IgG at room temperature for 2 hours and the reaction is subsequently stopped with 1/10 vol. of 0.1 M N-ethyl-maleimide. The conjugate is purified by gel chromatography (ACA 34, LKB) using 50 mmol/l TRIS/HCl, pH 7.4, and subsequently concentrated down to 1–3 mg/ml.

b) Preparation of an HIV 1 (env)-peptide-peroxidase conjugate 10 mg of HIV 1 (gp 41) peptide (IAF BioChem, Canada) are dissolved in 1 ml of glacial acetic acid/water (50:50, v/v). After neutralization with 5 N sodium hydroxide solution, a 10-fold molar excess of GMBS is added to the mixture, which is then incubated at room temperature for 1 h. The GMBS which remains unreacted is separated off by gel filtration (Sephadex G-25) using 0.1 M sodium phosphate/5 mmol/l NTA, pH 6.0. 10 mg of horseradish peroxidase are incubated in 5 ml of 10 mmol/l , sodium phosphate and 100 mmol/l NaCl, pH 8.0, with a 100-fold molar excess of 2-iminothiolane at room temperature for 1 h. Subsequently, free modifying reagent is removed by gel chromatography (Sephadex G-25) using 0.1 M sodium phosphate/5 mmol/l NTA, pH 6.0.

Both eluates (SH-activated peroxidase and maleimide-modified HIV 1 peptide) are combined and incubated at room temperature overnight. After the reaction has been stopped with 1/10 vol of 0.1 M N-ethylmaleimide, the conjugate is freed of non-reacted HIV 1 peptide by gel chromatography (Sephadex G-25). After concentration (2 mg/ml), the peptide-peroxidase conjugate is stored at −20° C.

c) 2-Step enzyme immunoassay for detecting HIV 1 antibodies

An enzyme immunoassay for detecting anti-HIV 1 antibodies is carried out as follows:

25 μl of sample buffer (0.3 M Tris/HCl and 1% albumin, 2% Tween 20, pH 7.2) are incubated with 100 μl of human serum at 37° C. for 30 min. in the wells of a test plate (®Enzygnost Anti HIV 1+2, Behringwerke AG, Marburg, FRG) coated wit HIV 1 and HIV 2 peptides. After washing 4 times with 50 mmol/l PBS, 0.1% Tween 20, 100 μl of the HIV 1 peptide-peroxidase conjugate (1:1000 in 0.1M Tris/

HCl, 1% albumin and 2% pluronic/F 64, pH 8.1) prepared according to Example 1 b) are pipetted in.

The 30-minute incubation (+37° C.) is terminated with 4 further washing steps. The bound peroxidase activity, which correlates directly with the number of bound HIV 1-specific antibodies, is determined by addition of $H_2O_2$ tetramethyl-benzidine (Behringwerke AG, Marburg, FRG).

d) Use of the reagent according to the invention

Anti-HIV 1 positive sera and anti-HIV negative sera are examined in the enzyme immunoassay according to c). In the one case, 10 μl of 50 mmol/l Tris/HCl, pH 7.4 (reference system), and in the other, 10 μl of the reagent prepared according to a) according to the invention (system according to the invention) are added to 10 ml of conjugate solution.

Figure 2:
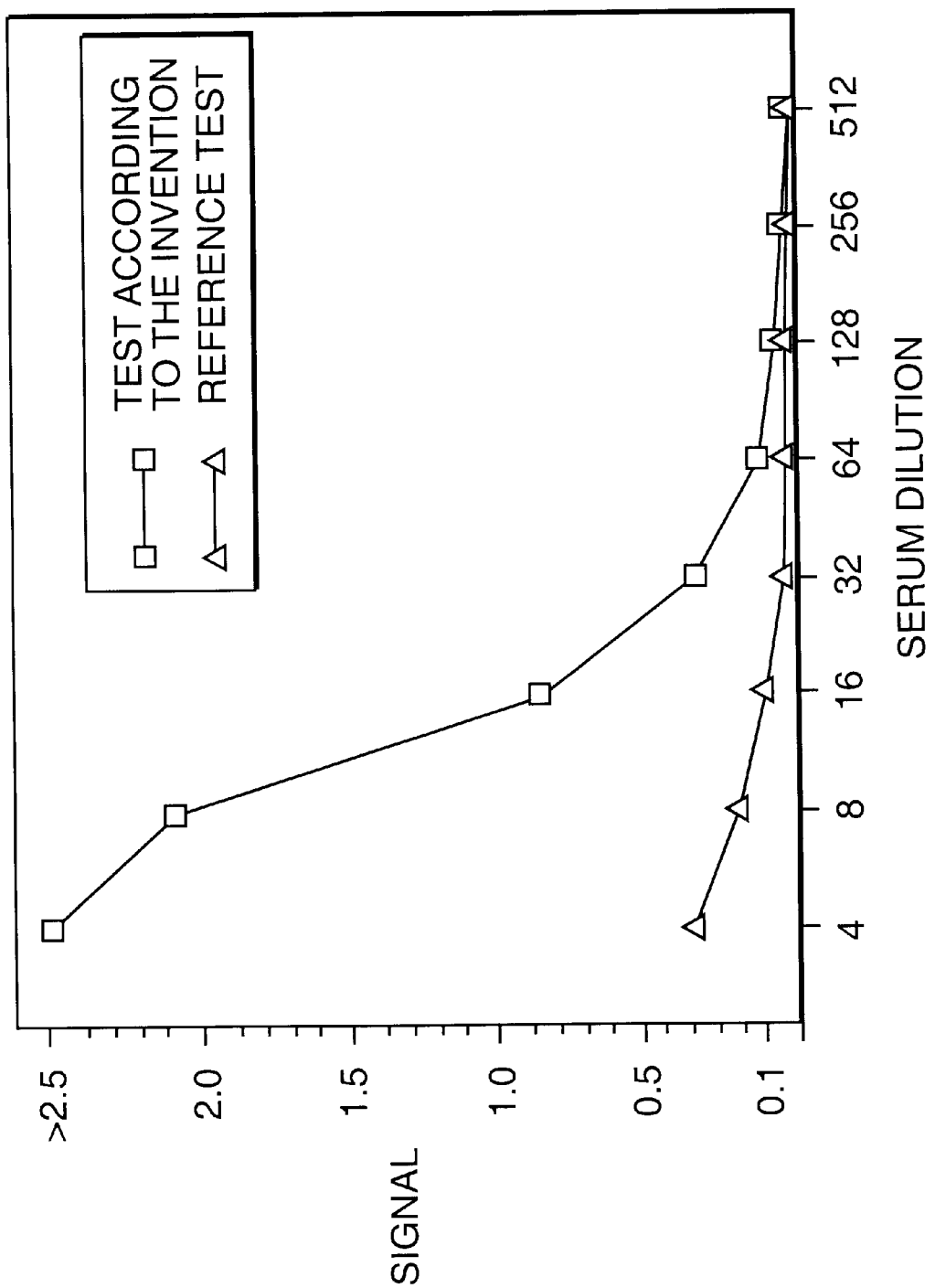
FIG. 2 depicts the titration curve of an anti-HIV 1 positive sample (#9804/109).

The results (extinction units) of the investigations are to be found in the table, and comparative titrations of HIV 1 antibodies of positive sera in FIG. 1 and FIG. 2.

TABLE

|  | Reference system | System according to the invention |
|---|---|---|
| Control serum, negative | 0.019 | 0.018 |
| Control serum, positive | 0.964 | 1.681 |
|  | 0.985 | 1.756 |
| Anti-HIV neg. sera | 0.015 | 0.019 |
|  | 0.017 | 0.021 |
|  | 0.032 | 0.028 |
|  | 0.019 | 0.024 |
|  | 0.030 | 0.018 |
| Anti-HIV neg. plasmas | 0.014 | 0.016 |
|  | 0.017 | 0.016 |
|  | 0.028 | 0.017 |
|  | 0.016 | 0.016 |
|  | 0.016 | 0.015 |
| Anti-HIV 1 pos. plasma | >2.500 | >2.500 |
| 1:500 | >2.500 | >2.500 |
| 1:1000 | 1.424 | 2.440 |
| 1:2000 | 0.694 | 1.054 |
| 1:4000 | 0.317 | 0.478 |
| 1:8000 | 0.161 | 0.216 |
| 1:16000 | 0.083 | 0.107 |
| 1:32000 | 0.052 | 0.064 |
| 1:64000 | 0.032 | 0.039 |
| Cut off value | 0.119 | 0.118 |

I claim:

1. A process for the determination of an analyte in a sample comprising the steps of:

(a) providing a solid support having immobilized thereon a first specific binding partner;

(b) reacting said solid support with said sample;

(c) adding to the resulting mixture of step (b) a further analyte specific binding partner which is directly or indirectly labeled;

(d) adding to the resulting mixture of step (b) or step (c) a binding factor having more than one site which specifically binds to the analyte, wherein said binding factor has no affinity for the immobilized first specific binding partner, is not labeled with the label used for signal formation in the process, and does not interfere with the immunochemical detection of the analyte; and (e) measuring the extent of the binding of the analyte to the first specific binding partner by means of the further analyte specific binding partner which bears a label.

2. A process as claimed in claim 1, wherein the analyte is an antigen.

3. A process as claimed in claim 2, wherein the analyte is an antibody.

4. The process of claim of claim 3, wherein the binding factor is an antibody that is specific for the Fc region of the analyte.

5. A process as claimed in claim 1, wherein the binding factor is a conjugated antibody.

6. A process as claimed in claim 1, wherein the binding factor is only added to the resulting mixture of step (c).

7. A process as claimed in claim 6, wherein the analyte is an antigen.

8. A process as claimed in claim 6, wherein the analyte is an antibody.

9. A process as claimed in claim 6, wherein the binding factor is a conjugated antibody.

* * * * *

UNITED STATES PATENT AND TRADEMARK OFFICE
CERTIFICATE OF CORRECTION

PATENT NO. : 5,914,243
DATED : June 22, 1999
INVENTOR(S) : Stefan Brust

It is certified that error appears in the above-identified patent and that said Letters Patent is hereby corrected as shown below:

Claim 3, Column 6, Line 25, "claim 2" should read --claim 1--;

Claim 4, Column 6, Line 27, after "process", delete "of claim" (first occurrence).

Signed and Sealed this

Eleventh Day of January, 2000

Attest:

Q. TODD DICKINSON

Attesting Officer

Acting Commissioner of Patents and Trademarks